US00PP33407P3

(12) United States Plant Patent
Bourne

(10) Patent No.: US PP33,407 P3
(45) Date of Patent: Aug. 31, 2021

(54) GRAPEVINE PLANT NAMED 'SV30-27-602'

(50) Latin Name: *Vitis vinifera*
Varietal Denomination: SV30-27-602

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 16/974,051

(22) Filed: Sep. 15, 2020

(65) Prior Publication Data

US 2021/0092889 P1 Mar. 25, 2021

Related U.S. Application Data

(60) Provisional application No. 62/973,256, filed on Sep. 24, 2019.

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./156, 205, 206
See application file for complete search history.

*Primary Examiner* — Susan McCormick Ewoldt
*Assistant Examiner* — Karen M Redden
(74) *Attorney, Agent, or Firm* — Eric C. Cole; Baker Manock & Jensen, PC

(57) ABSTRACT

A new and distinct variety of grapevine plant named 'SV30-27-602' particularly characterized by its red skinned large ellipsoidal shaped berries that have a distinct muscat flavor with no astringency.

2 Drawing Sheets

Latin name of the genus and species of the plant claimed: The plant claimed relates to a new and distinct variety of *Vitis vinifera*.

Variety denomination: The plant claimed shall be known as 'SV30-27-602'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV30-27-602'. As used herein, 'grapevine' refers to all plant parts including vines, canes, tendrils, leaves, fruit and roots of 'SV30-27-602'. Grapevine named 'SV30-27-602' is the result of an effort to produce a late ripening red, seedless table grape with fruit characteristics superior to currently available cultivar 'Scarlet Royal' (U.S. Plant Pat. No. 16,229). This cultivar resulted from a cross made in April 2009 between female grapevine named 'SV16-76-232' (unpatented) and male grapevine plant named 'SV21-66-226' (U.S. Plant Pat. No. 24,531). Resultant seeds were harvested in October 2009 and were stratified under refrigeration at 2 degrees Celsius. The seeds were planted in soil in the greenhouse in January 2010 and resultant seedlings were grown in the greenhouse until April 2010. The seedlings were transplanted to a field north of Delano, Calif. in that same month and were trained to a trellis that same year. Fruit of the seedling were observed on Aug. 9, 2013 at which time the selection for trialling was made. Woody cuttings were harvested in December of 2013 and buds of grapevine named 'SV30-27-602' were bench grafted to 'Freedom' (unpatented) rootstock. The resultant plants were planted in a trial location near McFarland, Calif. in May of 2014 and were trained to a t-trellis on 7 foot by 10 foot spacing. The present invention has been found to retain its distinctive characteristics through three successive asexual propagations.

Grapevine named 'SV30-27-602' differs from its female parent, grapevine named 'SV16-76-232' (unpatented), in that 'SV30-27-602' is stenospermocarpic with small seed traces while 'SV16-76-232' has fully developed, functional seeds.

Grapevine named 'SV30-27-602' differs from its male parent, 'SV21-66-226' (U.S. Plant Pat. No. 24,531), in that 'SV30-27-602' produces red skinned ellipsoidal grapes while 'SV21-66-226' produces green skinned grapes.

Grapevine named 'SV30-27-602' most closely resembles 'Scarlet Royal' (U.S. Plant Pat. No. 16,229) but it may be distinguished from 'Scarlet Royal' because 'SV30-27-60' produces berries with a much brighter red color than the dark red berries produced by 'Scarlet Royal'. Additionally, grapevine named 'SV30-27-602' produces berries with distinct muscat flavor and no astringency while 'Scarlet Royal' (U.S. Plant Pat. No. 16,229) berries develop astringency at full ripeness.

SUMMARY OF THE INVENTION

The following are the most outstanding and distinguishing characteristics of this new cultivar when grown under normal horticultural practices near McFarland, Calif.:

1. Red skinned berries;
2. Firm berry texture; and
3. Large, ellipsoidal shaped berries with muscat flavor.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from plants about 5 years old, grown in a field near McFarland, Calif. in 2019.

DETAILED BOTANICAL DESCRIPTION

Figure 1:
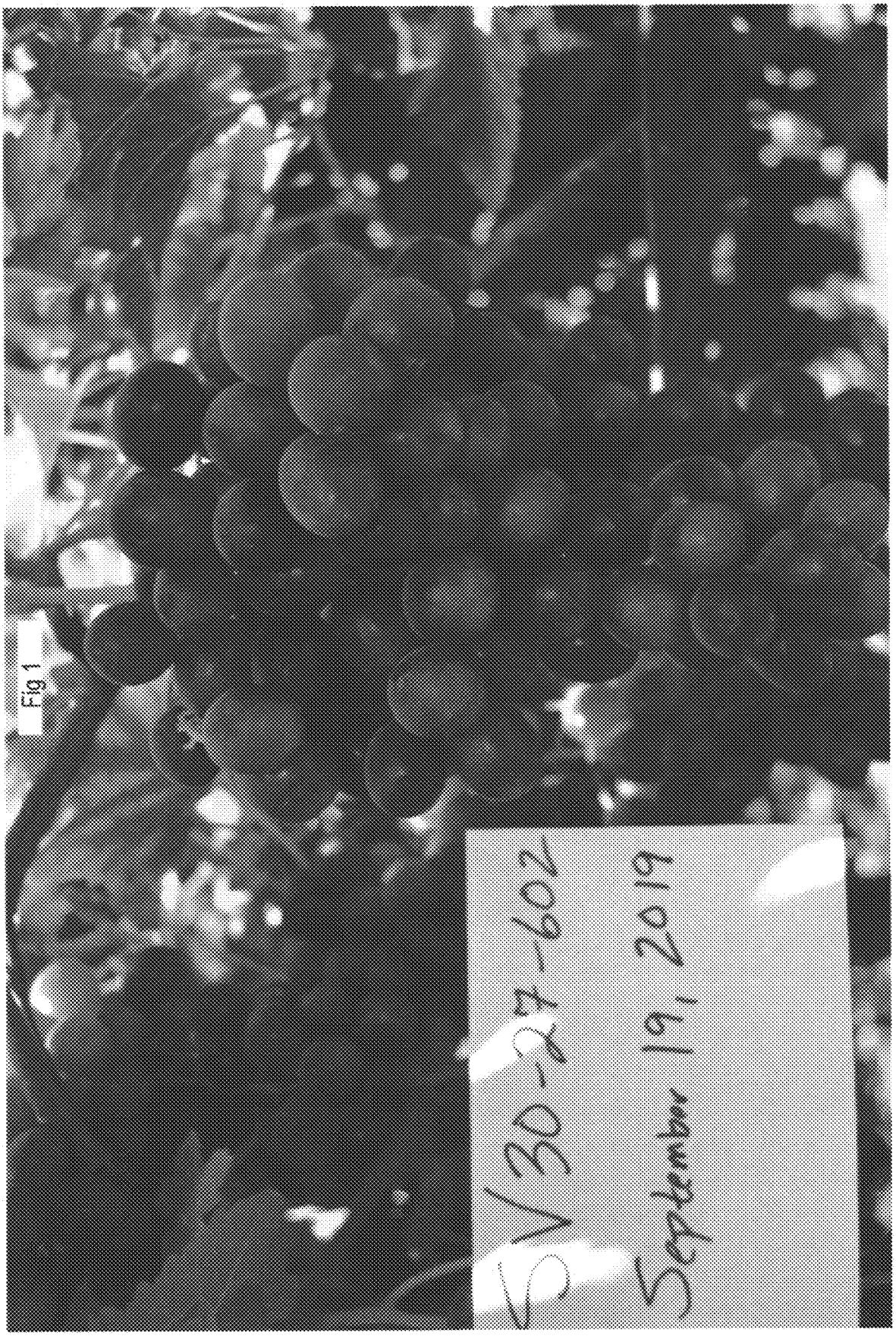
FIG. 1 Fruit cluster on vine treated with gibberellic acid, trunk girdling and ethephon.
Figure 2:
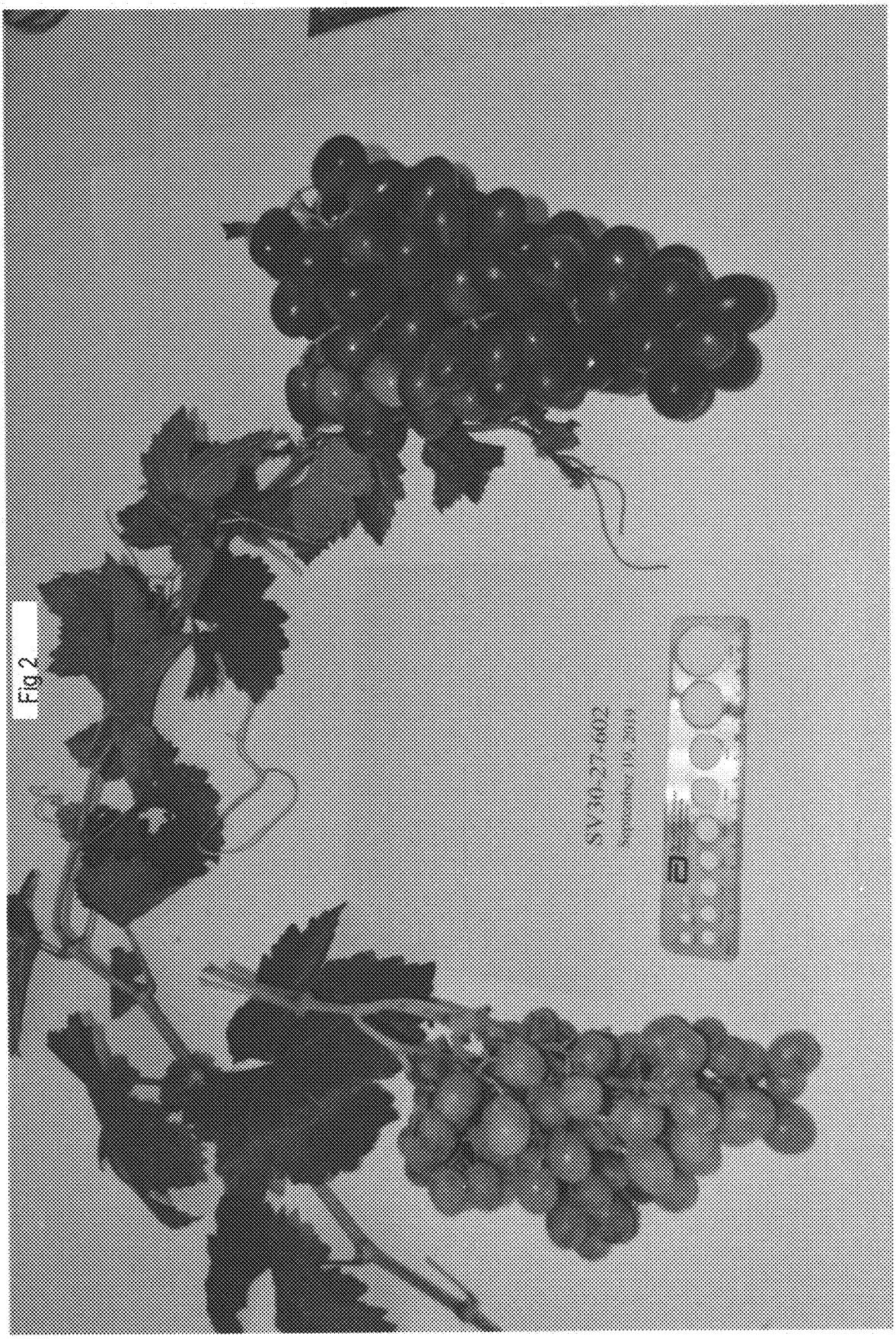
FIG. 2 Fruit cluster of natural fruit (left cluster) and fruit treated with gibberellic acid, trunk girdling and ethephon (right cluster) with a shoot bearing leaves and tendrils.

The following detailed description sets forth the distinctive characteristics of grapevine named 'SV30-27-602'. Descriptions of the new invention apply to vines of grapevine named 'SV30-27-602' grown on 'Freedom' (unpatented) rootstock at a density of 1,537 vines per hectare grown near McFarland, Calif. in 2019. These vines were in their fourth year of full production having been planted in 2014. These descriptions are believed to apply generally to the new variety grown under similar circumstances elsewhere. Color references are primarily to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties (UPOV) and published in *Descriptors for Grapevine* (*Vitis spp.*) (Anonymous, International Plant Genetic Resources Institute, 1997, ISBN 92-9043-352-3).

Classification:
- *Family*.—Vitaceae.
- *Botanical name*.—*Vitis vinifera*.
- *Variety name*.—'SV30-27-602'.

Flowers:
- *Flower sex*.—Perfect.
- *Position of first flowering nodes*.—Usually the 4th node.
- *Number of inflorescences per shoot*.—1 or 2.
- *Calyptra color*.—RHS Green group 143C.
- *Ovary length*.—2.5 mm.
- *Ovary width*.—1.0 mm.
- *Ovary color*.—*RHS Yellow green group* 144B.
- *Filament length*.—3.0 mm.
- *Filament color*.—Translucent, absence of pigmentation.
- *Anther length*.—0.5 mm.
- *Anther color*.—RHS Yellow group 10B.
- *Date of full bloom*.—May 15$^{th}$.

Growing tips:
- *Color*.—RHS Yellow green group N144A.
- *Anthocyanins*.—Absent.
- *Shape*.—Rounded.
- *Apex*.—Fully open.
- *Prostrate hair on tips*.—Sparse.
- *Anthocyanin coloration of prostrate hairs on tips*.—Absent.
- *Erect hairs on tip*.—Absent.

Young shoots:
- *Shoot attitude*.—Erect.
- *Color of dorsal side of internode*.—RHS Red purple group 60A and RHS Yellow green group 144B.
- *Color of ventral side of internode*.—RHS Yellow green group 144B.
- *Color of dorsal side of nodes*.—RHS Red purple group 60A and RHS Yellow green group 144B.
- *Color of ventral side of nodes*.—RHS Yellow green group 144B.
- *Erect hairs on internodes*.—Absent.

Tendrils:
- *Number*.—Bifurcated and trifurcated; forming at alternating nodes above the 6$^{th}$ or 7$^{th}$ node.
- *Length*.—15 cm to 29 cm averaging 21.9 cm.
- *Diameter*.—3 mm at base of tendril.
- *Texture*.—Smooth.
- *Color*.—RHS Yellow green group N144B.

Mature leaves:
- *Average blade length*.—14.2 cm.
- *Average blade width*.—18.9 cm.
- *Size of blade*.—Large.
- *Shape*.—Pentagonal.
- *Anthocyanin coloration of main veins on the upper side of the blade*.—Absent.
- *Mature leaf profile*.—Cupped upwards around entire margin.
- *Blistering* (*upper surface*).—Absent.
- *Leaf blade tip*.—In plane of blade.
- *Margins*.—Lobed, serrated, undulating.
- *Number of lobes*.—5.
- *Apex*.—Broadly acuminate.
- *Bases*.—Sagittate.
- *Thickness*.—Medium.
- *Undulation of blade between main and lateral veins*.—Slight.
- *Shape of teeth*.—Broadly conical, both sides convex.
- *Length of teeth*.—1 mm to 6 mm.
- *Ratio length/width of teeth*.—About 5:8.
- *General shape of petiole sinus*.—Open.
- *Tooth at petiole sinus*.—Absent.
- *Petiole sinus limited by veins*.—Absent.
- *Shape of upper lateral sinus*.—Closed.
- *Depth of upper lateral sinus*.—Deep.
- *Prostrate hairs between veins* (*lower surface*).—Absent.
- *Erect hairs between veins* (*lower surface*).—Absent.
- *Prostrate hairs on main veins* (*lower surface*).—Absent.
- *Density of erect hairs on main veins* (*lower surface*).—Sparse. Limited to junctions of large veins.
- *Prostrate hairs on main veins* (*upper surface*).—Absent.
- *Upper surface*.—Summer color: RHS Green group 137A. Surface texture: Smooth. Surface appearance: Smooth. Goffering of blade: Absent.
- *Lower surface*.—Summer color: RHS Green group 138A. Anthocyanin coloration of main veins on lower leaf surface: Absent. Anthocyanin coloration on laterals: Absent. Glossiness: Low. Pubescence distal portion of surface: Absent. Surface texture: Rough. Surface appearance: Dull.

*Petiole*.—Length: 12.3 cm. Length of petiole compared to middle vein: Slightly shorter. Density of prostrate hairs: Absent. Density of erect hairs: Absent. Color: In shade: RHS Yellow green group 144B. In sun: RHS Yellow green group 144B; some petioles with some anthocyanin development: RHS Red purple group 61C.

Fruit:

*Ripening period*.—Late mid-season at McFarland, Calif.

*Date of ripening*.—Sep. 19, 2019.

*Use*.—Fresh market.

*Keeping quality*.—Very good.

*Shipping quality*.—Good.

*Date of first harvest*.—Sep. 19, 2019.

*Solids-sugar*.—High, about 20 brix at full maturity.

*Refractometer test*.—18 brix.

*Bunch*.—Size: Medium. Length (peduncle excluded): Natural: About 25 cm. With gibberellic acid treatment: About 29 cm. Width: Natural: About 9 cm. With gibberellic acid treatment: About 13 cm. Cluster mass: Natural: 672.0 g. With gibberellic acid treatment: 1,190 g. Density: Well-filled, but loose. Number of berries: Natural: 129. With gibberellic acid treatment: 115. Form: Conical.

*Peduncle*.—Length: About 6 cm. Lignification: About half of peduncle length at full maturity. Color: RHS Yellow green 144C.

*Berry*.—Size: Large. Uniformity of size: Uniform. Weight. Natural, without gibberellic acid treatment: About 4.1 g. With gibberellic acid treatment: About 9.9 g. Shape: Natural, without gibberellic acid treatment: Ellipsoidal. With gibberellic acid treatment: Ellipsoidal. Presence of seeds: Natural: Seedless; most berries develop one or two small, soft rudimentary seeds about 5 mm in length. With gibberellic acid treatment: One or two small, soft rudimentary seeds about 1 mm. in length. Cross section: Circular. Dimensions: Natural: Length: About 2.2 cm. Width: About 1.9 cm. With gibberellic acid treatment: Length: About 3.3 cm. Width: About 2.2 cm. Skin color (without bloom): Natural: RHS Red purple 59B. With ethephon treatment: RHS Red purple 59A. Coloration of flesh: Translucent (no anthocyanin pigmentation). Juiciness of flesh: Very juicy. Berry firmness: Very firm. Particular flavor: Muscat. Bloom (cuticular wax): Weak. Pedicel length: About 1 cm. Berry separation from pedicel: With difficulty.

*Skin*.—Thickness: Medium. Texture: Crisp. Reticulation: Absent. Roughness: Absent. Tenacity: Tenacious to flesh. Tendency to crack: Resistant.

Plant:

*Vigor*.—Vigorous; vines spur-pruned and shoot thinned to 32 shoots producing 346 cm of growth per cane.

*Density of foliage*.—Medium, canopy allows a moderate amount of light on clusters.

*Productivity*.—Very productive. When spur pruned, up to 49,000 kg/hectare.

*Hardiness*.—Hardiness observed to 0° C.

*Rootstock*.—'Freedom' (unpatented).

Trunk:

*Shape*.—Broadly elliptical.

*Straps*.—Long, split.

*Surface texture*.—Shaggy.

*Trunk circumference*.—23.4 cm at 1.0 m of height on 6 year old plants.

*Inner bark color*.—RHS Greyed orange 175C.

*Outer bark color*.—RHS Grey 201B.

Woody shoot:

*Canes*.—Shape: Broadly elliptical. Internode length: About 10 cm. Width at node: 1.5 cm. Cross section: Elliptical. Surface: Smooth. Main color: RHS Greyed orange 167B. Lenticels: Inconspicuous.

*Laterals*.—Shape: Elliptical. Number: Laterals forming irregularly above node 4. Lateral growth is weak except where canes have been tipped. Most laterals terminate after forming 2 nodes. Length: About 2.5 cm. Diameter: About 6 mm. Internode length: About 1 cm. Color: RHS Yellow green 144B.

*Buds*.—Shape: Rounded with a slight point. Cane bud fruitfulness: Basal buds fruitful, usually 2 clusters per shoot. Length: 8 mm. Width: 5 mm. Height: 7 mm. Color: RHS Grey orange 175B.

Disease and insect resistance: No particular resistance or susceptibility has been observed. Normal disease control practices can be used.

Having thus described and illustrated our new variety of grapevine, I claim:

1. A new and distinct variety of grapevine plant named 'SV30-27-602', substantially as illustrated and described herein.

* * * * *